United States Patent [19]

Dudeck et al.

[11] 4,233,246
[45] Nov. 11, 1980

[54] MANUFACTURE OF ALIPHATIC HYDROXYCARBONYL COMPOUNDS ETHERIFIED WITH ALIPHATIC GROUPS

[75] Inventors: Christian Dudeck, Limburgerhof; Gunter Lehmann, Ludwigshafen; Norbert Petri, Frankenthal; Hans Diem, Mannheim; Werner Fliege, Otterstadt; Bernd Meissner, Heidelberg; Karl-Heinz Ross, Mutterstadt; Wolfgang Muehlthaler, Hemsbach, all of Fed. Rep. of Germany

[73] Assignee: BASF Aktiengesellschaft, Fed. Rep. of Germany

[21] Appl. No.: 971,416

[22] Filed: Dec. 20, 1978

[30] Foreign Application Priority Data

Dec. 24, 1977 [DE] Fed. Rep. of Germany ....... 2758124
Apr. 12, 1978 [DE] Fed. Rep. of Germany ....... 2815752

[51] Int. Cl.$^3$ ............................................. C07C 45/38
[52] U.S. Cl. .................................. 568/402; 252/476; 568/414; 568/471; 568/496
[58] Field of Search ....................... 260/594, 596, 602; 252/476

[56] References Cited

U.S. PATENT DOCUMENTS

| | | | |
|---|---|---|---|
| 2,170,855 | 8/1939 | Chitwood | 260/594 |
| 3,106,581 | 10/1963 | Neely | 260/596 |
| 3,941,811 | 3/1976 | Vignau | 260/596 |
| 3,948,997 | 4/1976 | Howe et al. | 252/476 |
| 3,956,184 | 5/1976 | Abramovich et al. | 252/476 |

*Primary Examiner*—Natalie Trousof
*Assistant Examiner*—James H. Reames
*Attorney, Agent, or Firm*—Keil & Witherspoon

[57] ABSTRACT

Aliphatic hydroxycarbonyl compounds etherified with aliphatic groups are prepared by oxidizing hydroxyalcohols in the presence of a metal catalyst which consists of one or more layers, each of a particular weight and each containing particles of a particular size, the catalyst bed also having a particular total thickness, and the catalyst components used being silver and copper, with or without added copper/tin/phosphorus or silver alone. The etherified hydroxyaldehydes and hydroxyketones obtainable by the process of the invention are valuable starting materials for the preparation of dyes, pesticides, plastics and scents.

12 Claims, 1 Drawing Figure

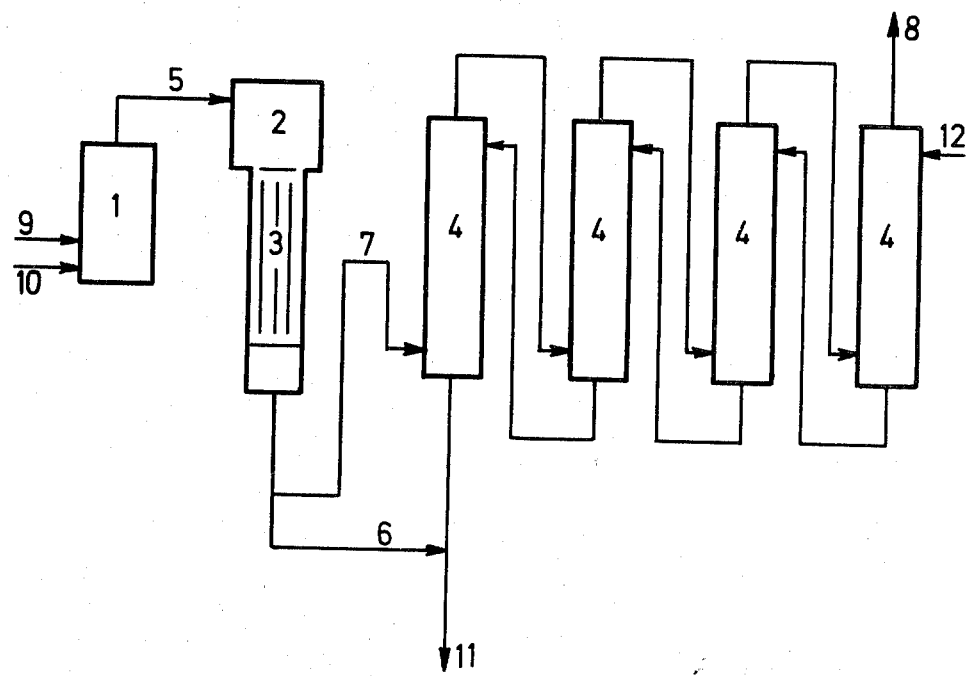

MANUFACTURE OF ALIPHATIC HYDROXYCARBONYL COMPOUNDS ETHERIFIED WITH ALIPHATIC GROUPS

The present invention relates to a novel process for the preparation of aliphatic hydroxycarbonyl compounds etherified with aliphatic groups by oxidizing hydroxyalcohols in the presence of a metal catalyst which consists of one or more layers, each of a particular weight and each containing particles of a particular size, the catalyst bed also having a particular total thickness, and the catalyst components used being silver and copper, with or without added copper/tin/phosphorus.

Houben-Weyl, Methoden der Organischen Chemie, volume 7/1, pages 166 and 167, discloses that compounds which in addition to the primary alcohol group contain ether groups in most cases give only very moderate yields when dehydrogenated to the aldehydes. To avoid decomposition reactions, it is necessary to work either at the lowest feasible temperature or, as in the case of the dehydrogenation of tetrahydrofurylcarbinol to tetrahydrofuran-2-aldehyde, to work at a relatively high temperature, with minimum residence time over the catalyst. Thus, when preparing methoxyacetaldehyde, a hydrogen-treated copper oxide catalyst and a reaction temperature of 300° C. are employed. Ethoxyacetaldehyde and butoxyacetaldehyde can also be prepared by a similar method, but in these cases the yields are even worse.

An article in Zh. Prikl. Khim. (Leningrad) 43 (1970), 1,132–1,136 (English text, pages 1,137–1,140), describes a reaction of methylglycol with air over silver wire spirals as a catalyst, at from 380° to 578° C., with yields of from 24.3 to 58 percent, based on starting material. Similar reactions were carried out with butylglycol at from 463° to 488° C. In both cases, reaction temperatures of from 465° to 475° C. are regarded as advantageous. A disadvantage of these processes is that notwithstanding the use of reduced pressure, and of equal amounts of nitrogen and air, the maximum achievable yield is only 58 percent.

It is also known (Houben-Weyl, loc. cit., volume 7/2a, pages 699–776) that secondary alcohols can be converted to ketones by catalytic dehydrogenation or by oxidation with air. The catalysts generally proposed are both hydrogenation catalysts and dehydrogenation catalysts, especially the above catalysts for the synthesis of aldehydes (loc. cit., page 700). In general, the dehydrogenation is carried out in the gas phase at from 180° to 400° C., in the main at from 200° to 250° C. In the synthesis of 1-methoxy-2-oxo-propane, oxidation with chromic acid/sulfuric acid/water mixtures gives a yield of only 29 percent (Houben-Weyl, loc. cit., volume 7/2a, pages 722–724).

U.S. Pat. No. 2,170,855 discloses that alkoxyisopropanols can be oxidized in the gas phase to alkoxyacetones by means of air in the presence of a metal oxide, eg. silver oxide, copper oxide, nickel oxide and cobalt oxide, or of a metal catalyst, eg. copper, copper/chromium, chromium, silver, cobalt and nickel. The reaction temperatures are stated to be from 250° to 300° C. If the process is carried out on an industrial scale, the yields obtained are from 9.8 to 33.7 percent.

All these processes are unsatisfactory in respect of simple and economical operation, yield and purity of the end product.

We have found that an aliphatic hydroxycarbonyl compound etherified with an aliphatic group may be obtained in an advantageous manner by catalytic oxidation of a hydroxyalcohol in the presence of a metal catalyst, if an aliphatic hydroxyalcohol, etherified with an aliphatic group, is oxidized, at from 450° to 700° C., in the presence of a catalyst which has a total thickness of from 5 to 100 millimeters and comprises (a) 3 or more layers of silver crystals, with some of the layers of silver crystals containing particles of size from 1 to 2.5 mm and constituting from 30 to 85 percent by weight of the catalyst, some of the layers of silver crystals containing particles of size from 0.75 to 1 mm and constituting from 2 to 30 percent by weight of the catalyst and the remainder of the layers of silver crystals containing particles of size from 0.2 to 0.75 mm and constituting from 8 to 50 percent by weight of the catalyst, and one or more layers of copper crystals containing particles of size from 0.2 to 0.75 mm and constituting from 1 to 40 percent by weight of the catalyst, or (b) 3 or more layers of silver crystals, with some of the layers of silver crystals containing particles of size from 1 to 2.5 mm and constituting from 30 to 85 percent by weight of the catalyst, some of the layers of silver crystals containing particles of size from 0.75 to 1 mm and constituting from 2 to 30 percent by weight of the catalyst and the remainder of the layers of silver crystals containing particles of size from 0.2 to 0.75 mm and constituting from 8 to 50 percent by weight of the catalyst, and one or more layers of copper crystals containing particles of size from 0.2 to 0.75 mm and constituting from 0.5 to 40 percent by weight of the catalyst, and one or more layers of catalyst particles comprising from 70 to 99 percent by weight of copper, from 0.9 to 20 percent by weight of tin and from 0.1 to 10 percent by weight of phosphorus, based on the total weight of these elements in these particles, with these layers of catalyst particles containing particles of size from 0.2 to 0.75 mm and constituting from 0.5 to 10 percent by weight of the catalyst, or (c) 3 or more layers of silver crystals, with some of the layers of silver crystals containing particles of size from 1 to 2.5 mm and constituting from 30 to 85 percent by weight of the catalyst, some of the layers of silver crystals containing particles of size from 0.75 to 1 mm and constituting from 2 to 30 percent by weight of the catalyst and the remainder of the layers of silver crystals containing particles of size from 0.2 to 0.75 mm and constituting from 13 to 68 percent by weight of the catalyst.

If methylglycol is used, the reaction can be represented by the following equation:

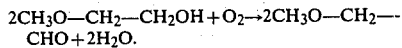

If 1,2-propylene glycol monomethyl ether (1-methoxy-2-hydroxypropane) is used, the reaction can be represented by the following equation:

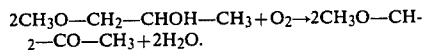

Compared to the prior art, the process of the invention surprisingly gives, more simply and more economically, a better overall result in respect of yield, space-time yield, purity of the end product and life of the catalyst. The latter is as a rule at least 30 days in the case of methoxyacetaldehyde. All these advantageous results are surprising in the light of the prior art, especially in the light of the disclosures in Houben-Weyl, because it would have been expected that the high temperatures used according to the invention would at least result in a substantial decrease in yield and substantial formation of decomposition products. Compared to the process described in Zh. Prikl. Khim., it is not necessary to employ water or an inert gas. The expensive method of working under reduced pressure, with special treatment of the catalyst, is avoided. It is possible to achieve high specific catalyst throughputs, for example 0.4–2.5 tonnes/m² of catalyst bed cross-section per hour, as against 0.15 tonne/m² of catalyst bed cross-section per hour in Zh. Prikl. Khim. Compared to the process described in U.S. Pat. No. 2,170,855, the yield and conversion are higher.

Advantageous end products, ie. aliphatic hydroxycarbonyl compounds etherified with aliphatic groups, are those of the formula

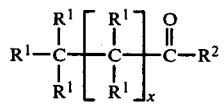   I and accordingly advantageous starting materials, ie. aliphatic hydroxyalcohols etherified with aliphatic groups, are those of the formula

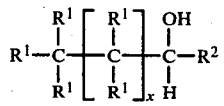   II where the individual radicals $R^1$ may be identical or different and each is hydrogen, an aliphatic radical or $R^3$—O—, but at least one radical $R^1$ is $R^3$—O—, $R^2$ is hydrogen or

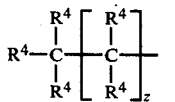

x and z may be identical or different and each is 0 or an integer, $R^3$ is an aliphatic radical, and the individual radicals $R^4$ may be identical or different and each is hydrogen, an aliphatic radical or $R^3$—O—, where $R^3$ has the above meaning. Preferred starting materials II and accordingly preferred end products I are those where the individual radicals $R^1$ are identical or different and each is hydrogen or alkyl or 1 to 5 carbon atoms or $R^3$—O—, but at least one radical $R^1$ is $R^3$—O—, $R^2$ is hydrogen or

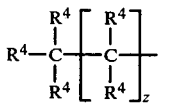

$R^3$ is alkyl of 1 to 5 carbon atoms, $R^4$ is hydrogen or alkyl of 1 to 5 carbon atoms or $R^3$—O—, where $R^3$ has the above preferred meaning, and x and z may be identical or different and each is 0 or an integer, especially 0, 1 or 2. If $R^2$ is hydrogen, x is 0, one radical $R^1$ is $R^3$—O— and another radical $R^1$ is hydrogen, the third radical $R^1$, in the case of embodiment (c), is preferably an aliphatic radical. The above radicals may in addition be substituted by groups which are inert under the reaction conditions, eg. alkyl of 1 to 4 carbon atoms.

Examples of starting materials II are methyl-, ethyl-, n-propyl-, isopropyl-, n-butyl-, sec.-butyl-, isobutyl- and tert.-butyl-ethylene glycol; the corresponding ethers of 1,2-propylene glycol, 1,3-propylene glycol, 1,2-butylene glycol, 1,3-butylene glycol, 2,3-butylene glycol, 1,4-butylene glycol, isobutylene glycol, 1,5-pentylene glycol and 1,6-hexylene glycol; ethanol, n-propanol, 2-hydroxypropane, n-butanol, 2-hydroxybutane and isobutanol substituted by 2 or 3 methoxy groups in an α-position relative to the hydroxyl group, and the corresponding diethyl-(α)-ethers and triethyl-(α)-ethers; and 2-hydroxypropane, 2-hydroxybutane, 2-hydroxypentane and 3-hydroxypentane suitably polysubstituted or, advantageously, monosubstituted, disubstituted or trisubstituted by methoxy, ethoxy, propoxy, isopropoxy, butoxy, tert.-butoxy, sec.-butoxy or isobutoxy in the α-, α'-, β-, β'-, α,α'-, β,β'-, α,β'- or β,α'-position relative to the hydroxyl group.

Either pure oxygen or gases containing free oxygen, especially air, may be used as the oxidizing agent. The oxygen, as a rule in the form of air, and the starting material II are advantageously employed in a molar ratio of from 0.25 to 0.8, especially from 0.35 to 0.6, mole of oxygen per mole of starting material II. The use of an inert gas is not essential but on the other hand also does not interfere with the reaction. If desired, the catalyst can be heated with a hot inert gas, advantageously nitrogen or combustion gases which have a low soot content and do not contain any catalyst poisons, such gases being, for example, at from 600° to 800° C.

The total thickness of the catalyst bed is from 5 to 100, preferably from 10 to 30, mm. In the catalyst of the reactor (the latter usually being set up vertically), the catalyst particles, in the form of silver crystals, are arranged, according to particle size, in an upper, middle and lower layer of the total bed. In general, the starting mixture of the vapor of starting material II and oxygen or air is passed downward through the bed, so that the upper layer or upper layers at the same time represent the part of the bed which faces the starting mixture. With reactors of different construction, or in the event of the starting mixture being passed through the reactor differently, all statements made in the description regarding the upper (lower) part of the catalyst apply similarly to the corresponding part which faces the starting mixture (or the reaction mixture being discharged); for example, in the case of a horizontal reactor these statements respectively apply to the front (rear) part of the catalyst. Data relating to the proportion, in percent by weight, of all catalyst particles relate to the total weight of the catalyst, ie. in the case of embodiment (a), to the weight of silver crystals and copper crystals, in the case of embodiment (b), to the copper/tin/phosphorus catalyst particles (Cu/Sn/P particles) and in the case of embodiment (c), to the silver crystals alone.

In embodiment (a), the following catalysts are used: the lower part of the bed of silver crystals comprises from 30 to 85, preferably from 50 to 78, percent by weight of all catalyst particles, the middle part of the silver crystal bed comprises from 2 to 30, preferably from 5 to 25, percent by weight of all catalyst particles and the upper part of the silver crystal bed comprises from 8 to 50, preferably from 13 to 35, percent by weight of all catalyst particles. The particles of the lower part of the bed have a size of from 1 to 2.5 mm, those of the middle part of the bed have a size of from 0.75 to 1 mm and those of the upper part of the bed have a size of from 0.2 to 0.75 mm. Each part of the silver crystal bed can consist of one or more layers, preferably of 1, 2 or 3 layers. The preferred catalyst comprises from 4 to 7, especially 4 or 5, layers of silver crystals. Each of these layers differs from the other in respect of the particle size of the silver crystals and in most cases also in respect of the proportion by weight, of the total catalyst bed, which it constitutes.

If the upper part of the silver crystal bed comprises 2 layers of silver crystals, the lower layer preferably constitutes from 4 to 46 percent by weight and has particles with a size of from 0.4 to 0.75 mm, whilst the upper layer correspondingly constitutes from 4 to 46 percent by weight and has particles of a size of from 0.2 to 0.4 mm. If the upper part of the silver crystal bed comprises 3 layers, the following are preferred in respect of the proportion by weight of the total catalyst (and the size of the particles): upper silver layer 3–45 percent by weight (0.2–0.4 mm); middle silver layer 3–45 percent by weight (0.4–0.6 mm); lower silver layer 2–44 percent by weight (0.6–0.75 mm). Accordingly, the following proportions by weight (size of particles) are preferred in the case of the middle part of the silver crystal bed:

(a) 2 layers of silver crystals: upper layer 1–29% by weight (0.75–0.9 mm); lower layer 1–29% by weight (0.9–1 mm).

(b) 3 layers of silver crystals: upper layer 0.7–28.7% by weight (0.75–0.8 mm); middle layer 0.7–28.7% by weight (0.8–0.9 mm); lower layer 0.6–28.6% by weight (0.9–1 mm).

In the case of the lower part of the silver crystal bed, the following are preferred:

(c) 2 layers of silver crystals: upper layer 15–70% by weight (1–1.75 mm); lower layer 15–70% by weight (1.75–2.5 mm).

(d) 3 layers of silver crystals: upper layer 10–65% by weight (1–1.5 mm); middle layer 10–65% by weight (1.5–2 mm); lower layer 10–65% by weight (2–2.5 mm).

The copper crystals in the catalyst are also arranged in layers. The number of layers of copper crystals can be greater than, equal to or, preferably, less than the number of layers of silver crystals. It is advantageous to employ one or 2—preferably one—layer of copper crystals. If only one such layer is used, it contains, in case (a), from 1 to 40, and in case (b), from 0.5 to 40, preferably, in both cases, from 2 to 30, percent by weight of all catalyst particles, the particle size being from 0.2 to 0.75 mm. If 2 layers of copper crystals are used, it is advantageous if the lower layer comprises from 0.5 to 39.5, preferably from 1 to 29, percent by weight of all catalyst particles and the upper layer comprises from 0.5 to 39.5, preferably from 1 to 29, percent by weight of all catalyst particles. The particles of the lower layer have sizes of from 0.4 to 0.75 mm and those in the upper layer of from 0.2 to 0.4 mm.

The layers of copper crystals can be arranged, as single layers, or as several layers together, above and/or below each layer of silver crystals. Advantageously, only one or 2 copper layers are used and are located above and/or below the upper part of the silver crystal bed. If the said upper part comprises several, advantageously 2 or 3, layers of silver crystals, it is preferred to use 2 layers of copper crystals, located respectively above and below the uppermost layer of the upper part of the silver crystal bed, or, more advantageously, to use only one layer of copper crystals, located above the uppermost layer of silver crystals.

The layering of each individual layer of silver crystals or layer of copper crystals and of each layer of Cu/Sn/P particles (if such are present) is in most cases uniform, so that the thickness of each individual layer is constant over its entire cross-section. In such cases, the thickness of the layer depends directly on the above proportions by weight, based on total catalyst, and on the particular size of the particles. However, all, or a plurality, or, advantageously, one, of the layers of silver crystals or copper crystals or Cu/Sn/P particles can also be layered nonuniformly; for example it is possible to introduce the bulk of the catalyst particles in the middle, at the sides or, advantageously, at the edge of the layer and accordingly to distribute only a smaller, residual amount over the remaining layer. In a preferred embodiment, several individual layers or, advantageously, one individual layer is introduced only at the edge of the catalyst zone, in the form of an annular or wreath-like layer, with a plane top and bottom surface, whilst the layer below each such annular layer is uniformly arranged and has a uniform arrangement. The following arrangement is advantageous: an annular layer is applied at the edge of the upper layer (layer 1) of the catalyst; advantageously, the diameter of the annular layer, ie. the difference in diameter between the cross-section of the total catalyst bed and the internal diameter of the annular layer, is from 1/100 to 1/10 of the catalyst diameter, and hence of the diameter of the upper, uniform layer. In a particularly preferred arrangement, such an annular layer is not applied on top of the upper layer (layer 1) but is located below it and hence on top of the next layer, ie. layer 2. In this way, the arrangement of annular layer plus layer 1, or annular layer, layer 1 and layer 2, assumes the shape of a flat dish with an upwardly curved rim. If the upper part of the bed comprises several layers, for example 2 or 3, the annular layer can be similarly located under any of the layers of the upper part of the bed, eg. under the layer 2 or layer 3. Since reaction tubes or tubular reaction chambers are usually employed as the reactor, such an edge arrangement rests against the inner wall of the tube.

In the case of embodiment (a), a particularly advantageous catalyst has the composition shown below, with layer 3 being an annular layer of silver crystals, the diameter of the ring being 1/60 of the catalyst diameter, and the ring being located under layer 2 and hence on top of layer 4:

Layer 1 (copper crystals): 10.7% by weight of the catalyst, particle size 0.2—0.4 mm Layer 2 (copper crystals): 10.3% by weight of the catalyst, particle size 0.4—0.75 mm Layer 3 (silver crystals): 13.4% by weight of the catalyst, particle size 0.2—0.75 mm Layer 4 (silver crystals): 5.3% by weight of the catalyst, particle size 0.75—1 mm Layer 5 (bottom layer) (silver crystals): 60.3% by weight of the catalyst, particle size 1—2.5 mm.

However, the preferred embodiment is (b). In this, 3 or more, preferably 3–9, layers of silver crystals, one or more, preferably one, layer of copper crystals, and one or more, preferably one, layer of Cu/Sn/P particles is used to assemble the complete catalyst.

In embodiment (b), one or more layers of Cu/Sn/P catalyst particles containing from 70 to 99 percent by weight of copper, from 0.9 to 20 percent by weight of tin and from 0.1 to 10 percent by weight of phosphorus, based on the combined weight of these elements in the particles, are used; it is advantageous to use 1 to 2 layers, especially one layer. Advantageously, one or 2 such layers are employed as the top layer or layers of the complete catalyst. Preferred catalyst particles contain from 90 to 97 percent by weight of copper, from 2.9 to 7 percent by weight of tin and from 0.1 to 3 percent by weight of phosphorus, based on the combined weight of these elements in the particles. The metals may be present as such or as their oxides and the phosphorus may be present as phosphoric acid, a phosphate or an oxide. Accordingly, the particles may consist of mixtures of the above elements and/or of mixtures of compounds, eg. phosphoric acid, copper oxide or tin oxide, with one another; advantageously, they are prepared in the conventional manner, for example by mixing the components, advantageously the above compounds, in a kneader. The above percentages by weight of the 3 components are calculated from the content of the 3 elements in the particles and are based on the total weight of the 3 elements in the particles, without reference to the actual chemical structure of the compounds or elements from which the particles are formed.

If only one layer is used, it constitutes from 0.5 to 10, preferably from 2 to 6, percent by weight of the complete catalyst, and contains particles of size from 0.2 to 0.75 mm. If 2 layers of Cu/Sn/P particles are used, the lower layer constitutes from 0.25 to 9.75, preferably from 1 to 5, percent by weight of all catalyst particles and the upper layer constitutes from 0.25 to 9.75, preferably from 1 to 5, percent by weight of all catalyst particles. The particles in the lower layer have a size of 0.4 to 0.75 mm and those in the upper layer from 0.2 to 0.4 mm. With regard to the beds, number of layers, arrangement, proportions by weight and particle sizes of the layers of silver crystals and copper crystals, the general and preferred values and data given above apply. The Tables which follow show preferred arrangements of the layers:

| Number of layers | Layer No. (counted from the top downward) | Contains Ag or Cu crystals or Cu/Sn/P particles | % by weight of the complete catalyst | | Particle size in mm | |
|---|---|---|---|---|---|---|
| | | | from | to | from | to |
| | 1 | Cu/Sn/P | 0.5 | 10 | 0.2 | 0.75 |
| | 2 | Cu | 0.5 | 40 | 0.2 | 0.75 |
| 5 | 3 | Ag | 8 | 50 | 0.2 | 0.75 |
| | 4 | Ag | 2 | 30 | 0.75 | 1 |
| | 5 | Ag | 30 | 85 | 1 | 2.5 |
| | 1 | Cu/Sn/P | 0.5 | 10 | 0.2 | 0.75 |
| | 2 | Cu | 0.5 | 40 | 0.2 | 0.75 |
| 6 | 3 | Ag | 8 | 50 | 0.2 | 0.75 |
| | 4 | Ag | 2 | 30 | 0.75 | 1 |
| | 5 | Ag | 15 | 70 | 1 | 1.75 |
| | 6 | Ag | 15 | 70 | 1.75 | 2.5 |
| | 1 | Cu/Sn/P | 0.5 | 10 | 0.2 | 0.75 |
| | 2 | Cu | 0.5 | 40 | 0.2 | 0.75 |
| 7 | 3 | Ag | 8 | 50 | 0.2 | 0.75 |
| | 4 | Ag | 1 | 29 | 0.75 | 0.9 |
| | 5 | Ag | 1 | 29 | 0.9 | 1.0 |
| | 6 | Ag | 15 | 70 | 1 | 1.75 |
| | 7 | Ag | 15 | 70 | 1.75 | 2.5 |
| | 1 | Cu/Sn/P | 0.5 | 10 | 0.2 | 0.75 |
| | 2 | Cu | 0.5 | 40 | 0.2 | 0.75 |
| | 3 | Ag | 8 | 50 | 0.2 | 0.75 |
| 8 | 4 | Ag | 1 | 29 | 0.75 | 0.9 |
| | 5 | Ag | 1 | 29 | 0.9 | 1 |
| | 6 | Ag | 10 | 65 | 1 | 1.5 |
| | 7 | Ag | 10 | 65 | 1.5 | 2 |
| | 8 | Ag | 10 | 65 | 2 | 2.5 |
| | 1 | Cu/Sn/P | 0.5 | 10 | 0.2 | 0.75 |
| | 2 | Cu | 0.5 | 40 | 0.2 | 0.75 |
| | 3 | Ag | 8 | 50 | 0.2 | 0.75 |
| 9 | 4 | Ag | 0.7 | 28.7 | 0.75 | 0.8 |
| | 5 | Ag | 0.7 | 28.7 | 0.8 | 0.9 |
| | 6 | Ag | 0.6 | 28.6 | 0.9 | 1 |
| | 7 | Ag | 10 | 65 | 1 | 1.5 |
| | 8 | Ag | 10 | 65 | 1.5 | 2 |
| | 9 | Ag | 10 | 65 | 2 | 2.5 |
| | 1 | Cu/Sn/P | 0.5 | 10 | 0.2 | 0.75 |
| | 2 | Cu | 0.5 | 40 | 0.2 | 0.75 |
| | 3 | Ag | 4 | 46 | 0.2 | 0.4 |
| | 4 | Ag | 4 | 46 | 0.4 | 0.75 |
| 10 | 5 | Ag | 0.7 | 28.7 | 0.75 | 0.8 |
| | 6 | Ag | 0.7 | 28.7 | 0.8 | 0.9 |
| | 7 | Ag | 0.6 | 28.6 | 0.9 | 1 |
| | 8 | Ag | 10 | 65 | 1 | 1.5 |
| | 9 | Ag | 10 | 65 | 1.5 | 2 |
| | 10 | Ag | 10 | 65 | 2 | 2.5 |
| | 1 | Cu/Sn/P | 0.5 | 10 | 0.2 | 0.75 |
| | 2 | Cu | 0.5 | 40 | 0.2 | 0.75 |
| | 3 | Ag | 3 | 45 | 0.2 | 0.4 |
| | 4 | Ag | 3 | 45 | 0.4 | 0.6 |

-continued

| Number of layers | Layer No. (counted from the top downward) | Contains Ag or Cu crystals or Cu/Sn/P particles | % by weight of the complete catalyst from | to | Particle size in mm from | to |
|---|---|---|---|---|---|---|
| 11 | 5 | Ag | 2 | 44 | 0.6 | 0.75 |
|  | 6 | Ag | 0.7 | 28.7 | 0.75 | 0.8 |
|  | 7 | Ag | 0.7 | 28.7 | 0.8 | 0.9 |
|  | 8 | Ag | 0.6 | 28.6 | 0.9 | 1 |
|  | 9 | Ag | 10 | 65 | 1 | 1.5 |
|  | 10 | Ag | 10 | 65 | 1.5 | 2 |
|  | 11 | Ag | 10 | 65 | 2 | 2.5 |
|  | 1 | Cu/Sn/P | 0.5 | 10 | 0.2 | 0.75 |
|  | 2 | Cu | 0.5 | 39.5 | 0.2 | 0.4 |
|  | 3 | Cu | 0.5 | 39.5 | 0.4 | 0.75 |
|  | 4 | Ag | 3 | 45 | 0.2 | 0.4 |
|  | 5 | Ag | 3 | 45 | 0.4 | 0.6 |
| 12 | 6 | Ag | 2 | 44 | 0.6 | 0.75 |
|  | 7 | Ag | 0.7 | 28.7 | 0.75 | 0.8 |
|  | 8 | Ag | 0.7 | 28.7 | 0.8 | 0.9 |
|  | 9 | Ag | 0.6 | 28.6 | 0.9 | 1 |
|  | 10 | Ag | 10 | 65 | 1 | 1.5 |
|  | 11 | Ag | 10 | 65 | 1.5 | 2 |
|  | 12 | Ag | 10 | 65 | 2 | 2.5 |
|  | 1 | Cu/Sn/P | 0.25 | 9.75 | 0.2 | 0.4 |
|  | 2 | Cu/Sn/P | 0.25 | 9.75 | 0.4 | 0.75 |
|  | 3 | Cu | 0.5 | 39.5 | 0.2 | 0.4 |
|  | 4 | Cu | 0.5 | 39.5 | 0.4 | 0.75 |
| 13 | 5 | Ag | 3 | 45 | 0.2 | 0.4 |
|  | 6 | Ag | 3 | 45 | 0.4 | 0.6 |
|  | 7 | Ag | 2 | 44 | 0.6 | 0.75 |
|  | 8 | Ag | 0.7 | 28.7 | 0.75 | 0.8 |
|  | 9 | Ag | 0.7 | 28.7 | 0.8 | 0.9 |
|  | 10 | Ag | 0.6 | 28.6 | 0.9 | 1 |
|  | 11 | Ag | 10 | 65 | 1 | 1.5 |
|  | 12 | Ag | 10 | 65 | 1.5 | 2 |
|  | 13 | Ag | 10 | 65 | 2 | 2.5 |

In the case of embodiments (a) and (b), the above catalyst arrangements with 5, 6 and 7 layers are particularly preferred.

In embodiment (c), the following catalysts are used: the lower part of the bed of silver crystals comprises from 30 to 85, preferably from 50 to 78, percent by weight of all catalyst particles, the middle part of the silver crystal bed comprises from 2 to 30, preferably from 5 to 25, percent by weight of all catalyst particles and the upper part of the silver crystal bed comprises from 13 to 68, preferably from 17 to 45, percent by weight of all catalyst particles. The particles of the lower part of the bed have a size of from 1 to 2.5 mm, those of the middle part of the bed have a size of from 0.75 to 1 mm and those of the upper part of the bed have a size of from 0.2 to 0.75 mm. Each part of the silver crystal bed can consist of one or more layers, preferably of 1, 2 or 3 layers. The preferred catalyst comprises from 4 to 7, especially 4 to 5, layers of silver crystals. Each of these layers differs from the other in respect of the particle size of the silver crystals and in most cases also in respect of the proportion by weight, of the total catalyst bed, which it constitutes.

If the upper part of the silver crystal bed comprises 2 layers of silver crystals, the lower layer preferably constitutes from 6.5 to 61.5 percent by weight and has particles with a size of from 0.4 to 0.75 mm, whilst the upper layer correspondingly constitutes from 6.5 to 61.5 percent by weight and has particles of a size of from 0.2 to 0.4 mm. If the upper part of the silver catalyst bed comprises 3 layers, the following are preferred in respect of the proportion by weight of the total catalyst (and the size of the particles): upper silver layer 4–59 percent by weight (0.2–0.4 mm); middle silver layer 4–59 percent by weight (0.4–0.6 mm); lower silver layer 5–60 percent by weight (0.6–0.75 mm). Accordingly, the following proportions by weight (size of particles) are preferred in the case of the middle part of the silver crystal bed:

(a) 2 layers of silver crystals: upper layer 1—29% by weight (0.75–0.9 mm); lower layer 1—29% by weight (0.9–1 mm).

(b) 3 layers of silver crystals: upper layer 0.7—28.7% by weight (0.75–0.8 mm); middle layer 0.7—28.7% by weight (0.8–0.9 mm); lower layer 0.6—28.6% by weight (0.9–1 mm).

In the case of the lower part of the silver crystal bed, the following are preferred:

(c) 2 layers of silver crystals: upper layer 15—70% by weight (1–1.75 mm); lower layer 15—70% by weight (1.75–2.5 mm).

(d) 3 layers of silver crystals: upper layer 10—65% by weight (1–1.5 mm); middle layer 10—65% by weight (1.5–2 mm); lower layer 10—65% by weight (2–2.5 mm).

A particularly advantageous catalyst has the following composition:

Layer 1 (top layer): 6.5–61.5% by weight of the catalyst, with particles of size 0.2–0.4 mm Layer 2: 6.5–61.5% by weight of the catalyst, with particles of size 0.4–0.75 mm Layer 3: 1–29% by weight of the catalyst, with particles of size 0.75–0.9 mm Layer 4: 1–29% by weight of the catalyst, with particles of size 0.9–1 m Layer 5: 15–70% by weight of the catalyst, with particles of size 1–1.75 mm Layer 6 (bottom layer): 15–70% by weight of the catalyst, with particles of size 1.75–2.5 mm.

Advantageously, from 0.2 to 2.5 tonnes, especially from 0.6 to 2 tonnes, of starting material II, in vapor form, is passed through the catalyst per m² of catalyst bed cross-section per hour. In industrial operation, the catalyst bed diameter is preferably at least 0.05, advantageously from 0.1 to 3, meters. Advantageous residence times are from 0.001 to 1 minute, in the case of the preparation of methoxyacetaldehyde, using catalyst embodiment (a) or (b), preferably from 0.01 to 0.6 minute, and in the case of the preparation of methoxyacetone preferably from 0.01 to 0.5 minute. The residence time relates to, and is calculated on the basis of, the volume of the reaction zone without catalyst charge. For example, the reaction space of an empty reaction tube can serve as the basis of calculation.

The reaction is advantageously carried out at from 450° to 700° C., preferably at from 475° to 650° C., especially at from 500° to 625° C., under atmospheric or superatmospheric pressure, batchwise or preferably continuously. It can be carried out in the absence of any added solvent, but it is desirable to use water, advantageously in an amount of from 5 to 40, especially from 10 to 20, percent by weight based on starting material II. Equally, by-products of the preparation of the starting material II may still be present in the latter, for example in an amount of up to 10 percent by weight, based on II.

The oxidation may be carried out as follows: the starting material II, with or without water, is introduced into an evaporator, eg. a falling film evaporator, and is vaporized, advantageously at from 70° to 180° C., if water is used. The materials are introduced either individually or as a mixture. The gaseous mixture of starting material II in vapor form and air with or without inert gas, and steam, in the above amounts, is then passed through the catalyst at the reaction temperature. The process is in general carried out continuously, under pressures of from 0.5 to 3 bar, preferably from 0.8 to 1.8 bar. Advantageously, the silver catalyst is heated to 250°–500° C., preferably 380°–450° C., before starting the process. The start of the exothermic reaction can advantageously be ascertained by adding air to the starting mixture and observing the temperature change in the catalyst. If the reaction starts, an immediate rise in temperature is observed; if it does not start, the introduction of the cold air lowers the temperature. The temperature in the catalyst is advantageously measured by thermocouples. When the reaction has started, air is in general fed continuously into the vapor of the starting mixture, where appropriate by passing the air through the still of the evaporator. It is advantageous to cool the reaction gases, leaving the catalyst zone, rapidly, for example to 20°–160° C. This condenses the greater part of the end product I. The cooled gas mixture is then advantageously fed to an absorption tower in which the remainder of the end product I is washed out of the gas mixture with a suitable solvent, eg. dimethylformamide, dimethylsulfoxide, acetone, methanol, water or a mixture of these and/or previously collected condensate; advantageously, washing is carried out in counter-current. The end product I is then isolated from the condensate and the absorbates in the conventional manner, for example by distillation.

The etherified hydroxyaldehydes and hydroxyketones obtainable by the process of the invention are valuable starting materials for the preparation of dyes, pesticides, plastics and scents. Regarding their use, reference may be made to the publications cited earlier.

In the Examples which follow, parts are by weight.

EXAMPLE 1 (DRAWING)

An installation comprising an evaporator (1), a vertical tubular reactor (2), a downstream cooler (3) and an absorption installation (4) is used. The evaporator is connected to the tubular reactor by means of line (5). This line can be heated up to where it joins the reactor. The catalyst bed is located below the reactor top and is followed by the cooling zone (3) connected to the absorption installation (4) by means of line (7). The condensate formed in the cooling zone (3) is fed to line (11) via line (6). The absorption installation (4) comprises four absorption columns, with cooling, arranged as a cascade. These four columns are packed with 15 mm Pall ceramic rings. The off-gas escapes through line (8).

A catalyst (1.63 parts) of silver crystals (Ag), copper crystals (Cu) and Cu/Sn/P catalyst particles (94.1 percent by weight of Cu, 4.9 percent by weight of Sn, 1 percent by weight of P) is arranged as follows in the reactor (2):

| | Type of particles | Proportion of complete catalyst Percent by weight | Particle size mm |
|---|---|---|---|
| Layer 1 (top) | Cu/Sn/P | 2.7 | 0.2 – 0.75 |
| Layer 2 | Cu | 18.8 | 0.2 – 0.75 |
| Layer 3 | Ag | 13.2 | 0.2 – 0.75 |
| Layer 4 | Ag | 14.7 | 0.75 – 1.0 |
| Layer 5 (bottom) | Ag | 50.6 | 1.0 – 2.5 |

The diameter of the catalyst bed is 0.15 meter and the total thickness of the catalyst bed before starting the reaction is 22 millimeters.

The catalyst is heated to 380° C., by passing hot nitrogen through it. In the evaporator, 15 parts of ethylene glycol monomethyl ether are introduced through line (10) and heated to 80° C. 0.95 part of air per hour is then passed into the evaporator through line (9) and the contents of the evaporator are heated further, to 110° C. The amount of air is then increased to 1.4 parts per hour, whereupon the temperature of the catalyst begins to rise. The reaction having started, as indicated by the rising catalyst temperature, the following adjustments are made in the course of 3 hours: the nitrogen feed is stopped, the air feed is brought to 14.6 parts/hour, at the same time the amount of ethylene glycol monomethyl ether introduced via line (10), evaporator (1) and line (5) and passed through the catalyst, is brought to 14.1 parts per hour (corresponding to a throughput of 0.8 tonne of ethylene glycol monomethyl ether per hour per square meter of catalyst bed cross-section), and 9.3 parts of water per hour are added. The pressure in front of the catalyst is 1.04 bar, and the catalyst assumes a temperature of 575° C. The reaction mixture is subsequently cooled to 94° C. in the cooling zone (3) of the reactor. The absorption (4) is carried out in 4 stages, as a counter-current gas scrubbing operation. The absorption liquid employed consists of 11.5 parts of water per hour, at 25° C., introduced into the cascade (4) via line (12). 10,152 parts of ethylene glycol monomethyl ether are passed over the catalyst in the course of 720 hours. A total of 2,274 parts of unconverted ethylene glycol monomethyl ether and 5,860 parts of methoxyacetaldehyde are obtained via line (11). The conversion is 77.6 percent and the yield of methoxyacetaldehyde is 76.4% of theory, based on ethylene glycol monomethyl ether converted.

EXAMPLE 2

Using the method described in Example 1, a mixture of 56.3 parts of 1,2-propylene glycol monomethyl ether and 14.1 parts of water with 58.5 parts of air is passed in the course of 5 hours, at 600° C., and 1.09 bar, over 0.79 part of a catalyst having the following composition:

|  | Type of particles | Proportion of complete catalyst (% by weight) | Particle size mm |
|---|---|---|---|
| Layer 1 (top) | Cu | 2.5 | 0.2 – 0.75 |
| Layer 2 | Ag | 12 | 0.2 – 0.4 |
| Layer 3 | Ag | 12.5 | 0.4 – 0.75 |
| Layer 4 | Ag | 6 | 0.75 – 0.9 |
| Layer 5 | Ag | 6 | 0.9 – 1.0 |
| Layer 6 | Ag | 30 | 1 – 1.75 |
| Layer 7 (bottom) | Ag | 31 | 1.75 – 2.5 |

0.34 part of unconverted propylene glycol monomethyl ether and 38.25 parts of methoxyacetone are obtained. The conversion is 99.4 percent and the yield of methoxyacetone is 69.9% of theory, based on propylene glycol monomethyl ether converted.

EXAMPLE 3

An installation comprising an evaporator, a vertical tubular reactor connected thereto, a downstream cooler and an absorption installation is used. The catalyst bed is located below the reactor top, and below the catalyst bed is the cooling zone connected by a line to the absorption installation.

0.79 part of a catalyst of silver crystals, made up as shown below, is introduced into the reactor:

|  | Proportion of complete catalyst (% by weight) | Particle size mm |
|---|---|---|
| Layer 1 (top) | 14.5 | 0.2–0.4 |
| Layer 2 | 12.5 | 0.4–0.75 |
| Layer 3 | 6 | 0.75–0.9 |
| Layer 4 | 6 | 0.9–1.0 |
| Layer 5 | 30 | 1–1.75 |
| Layer 6 (bottom) | 31 | 1.75–2.5 |

The diameter of the catalyst bed is 0.15 meter and the total thickness of the catalyst bed before starting the reaction is 22 millimeters.

In the evaporator, 11.26 parts of 1,2-propylene glycol monomethyl ether and 2.82 parts of water are evaporated per hour, at 110° C. 11.7 parts of air are passed per hour through the evaporator. The vapor/air mixture is passed over the catalyst. The throughput is 0.64 tonne of 1,2-propylene glycol monomethyl ether per hour per square meter of catalyst bed cross-section. The reaction is carried out with a pressure, in front of the catalyst, of 1.03 bar and at a catalyst temperature of 600° C. The reaction mixture is subsequently cooled to 40° C. in the cooling zone of the reactor. The absorption itself is carried out in 4 stages in counter-current, in the form of a gas scrubbing operation. The absorption liquid used consists of 11.5 parts per hour of water at 25° C., introduced into the absorption installation. Per hour, a total of 0.068 part of unconverted 1,2-propylene glycol monomethyl ether and 9.84 parts of methoxyacetone are obtained. The conversion is 99.4 percent and the yield of methoxyacetone is 89.4% of theory, based on 1,2-propylene glycol monomethyl ether employed.

We claim:

1. A process for the preparation of an aliphatic hydroxycarbonyl compound etherified with an aliphatic group, by catalytic oxidation of an etherified hydroxyalcohol in the presence of a metal catalyst, wherein an aliphatic hydroxyalcohol, etherified with an aliphatic group, is oxidized with an oxygen-containing gas, at from 450° to 700° C., in the presence of a catalyst arranged according to particle size in an upper or front region, middle region and a lower or rear region which have a total thickness of from 5 to 100 millimeters and comprise:
   (a) at least three layers of silver crystals of different particle size, with at least one of the layers of silver crystals constituting the lower or rear region of the catalyst from which the oxidized mixture is discharged containing particles of size from 1 to 2.5 mm and constituting from 30 to 85 percent by weight of the catalyst, at least one of the layers of silver crystals constituting the middle region of the catalyst containing particles of size from 0.75 to 1 mm and constituting from 2 to 30 percent by weight of the catalyst and at least one of the layers of silver crystals constituting the upper or front region of the catalyst facing the mixture to be oxidized containing particles of size from 0.2 to 0.75 mm and constituting from 8 to 50 percent by weight of the catalyst, and at least one layer of copper crystals arranged above or below one of said layers of silver crystals and containing particles of size from 0.2 to 0.75 mm and constituting from 1 to 40 percent by weight of the catalyst, or
   (b) at least three layers of silver crystals of different particle size, with at least one of the layers of silver crystals constituting the lower or rear region of the catalyst from which the oxidized mixture is discharged containing particles of size from 1 to 2.5 mm and constituting from 30 to 85 percent by weight of the catalyst, at least one of the layers of silver crystals constituting the middle region of the catalyst containing particles of size from 0.75 to 1 mm and constituting from 2 to 30 percent by weight of the catalyst and at least one of the layers of silver crystals constituting the upper or front region of the catalyst facing the mixture to be oxidized containing particles of size from 0.2 to 0.75 mm and constituting from 8 to 50 percent by weight of the catalyst, and at least one layer of copper crystals arranged above or below one of said layers of silver crystals containing particles of size from 0.2 to 0.75 mm and constituting from 0.5 to 40 percent by weight of the catalyst, and at least one layer of catalyst particles comprising from 70 to 99 percent by weight of copper, from 0.9 to 20 percent by weight of tin and from 0.1 to 10 percent by weight of phosphorus, based on the total weight of these elements in these particles, with these layers of catalyst particles containing particles of size from 0.2 to 0.75 mm and constituting from 0.5 to 10 percent by weight of the catalyst, or
   (c) at least three layers of silver crystals of different particle size, with at least one of the layers of silver crystals constituting the lower or rear region of the catalyst from which the oxidized mixture is discharged containing particles of size from 1 to 2.5 mm and constituting from 30 to 85 percent by weight of the catalyst, at least one of the layers of silver crystals constituting the middle region of the catalyst containing particles of size from 0.75 to 1 mm and constituting from 2 to 30 percent by weight of the catalyst and at least one of the layers of silver crystals constituting the upper or front region of the catalyst facing the mixture to be oxidized containing particles of size from 0.2 to 0.75 mm and constituting from 13 to 68 percent by weight of the catalyst.

2. A process as set forth in claim 1, wherein the oxidation is carried out in the molar ratio of from 0.25 to 0.8 mole of oxygen per mole of starting material.

3. A process as set forth in claim 1, wherein the oxidation is carried out with a total catalyst bed thickness of from 10 to 30 mm.

4. A process as set forth in claim 1, wherein the oxidation is carried out with from 0.2 to 2.5 tonnes of starting material, in vapor form, per $m^2$ of catalyst bed cross-section per hour.

5. A process as set forth in claim 1, wherein the oxidation is carried out with a residence time of from 0.001 to 1 minute.

6. A process as set forth in claim 1, wherein the oxidation is carried out at from 475° to 650° C.

7. A process as set forth in claim 1, wherein the oxidation is carried out at from 500° to 625° C.

8. A process as set forth in claim 1, wherein the oxidation is carried out with from 5 to 40 percent by weight of water, based on starting material.

9. A process as set forth in claim 1, wherein the oxidation is carried out at a pressure of from 0.5 to 3 bar.

10. A process as set forth in claim 1 in which said catalyst consists essentially of
at least three layers of silver crystals of different particle size, with at least one of the layers of silver crystals constituting the lower or rear region of the catalyst from which the oxidized mixture is discharged containing particles of size from 1 to 2.5 mm and constituting from 30 to 85 percent by weight of the catalyst, at least one of the layers of silver crystals constituting the middle region of the catalyst containing particles of size from 0.75 to 1 mm and constituting from 2 to 30 percent by weight of the catalyst and at least one of the layers of silver crystals constituting the upper or front region of the catalyst facing the mixture to be oxidized containing particles of size from 0.2 to 0.75 mm and constituting from 8 to 50 percent by weight of the catalyst, and at least one layer of copper crystals arranged above or below one of said layers of silver crystals and containing particles of size from 0.2 to 0.75 mm and constituting from 1 to 40 percent by weight of the catalyst.

11. A process as set forth in claim 1 in which said catalyst consists essentially of
at least three layers of silver crystals of different particle size, with at least one of the layers of silver crystals constituting the lower or rear region of the catalyst from which the oxidized mixture is discharged containing particles of size from 1 to 2.5 mm and constituting from 30 to 85 percent by weight of the catalyst, at least one of the layers of silver crystals constituting the middle region of the catalyst containing particles of size from 0.75 to 1 mm and constituting from 2 to 30 percent by weight of the catalyst and at least one of the layers of silver crystals constituting the upper or front region of the catalyst facing the mixture to be oxidized containing particles of size from 0.2 to 0.75 mm and constituting from 8 to 50 percent by weight of the catalyst, and at least one layer of copper crystals arranged above or below one of said layers of silver crystals and containing particles of size from 0.2 to 0.75 mm and constituting from 0.5 to 40 percent by weight of the catalyst, and at least one layer of catalyst particles comprising from 70 to 99 percent by weight of copper, from 0.9 to 20 percent by weight of tin and from 0.1 to 10 percent by weight of phosphorus, based on the total weight of these elements in these particles, with these layers of catalyst particles containing particles of size from 0.2 to 0.75 mm and constituting from 0.5 to 10 percent by weight of the catalyst.

12. A process as set forth in claim 1 in which said catalyst consists essentially of
at least three layers of silver crystals of different particle size, with at least one of the layers of silver crystals constituting the lower or rear region of the catalyst from which the oxidized mixture is discharged containing particles of size from 1 to 2.5 mm and constituting from 30 to 85 percent by weight of the catalyst, at least one of the layers of silver crystals constituting the middle region of the catalyst containing particles of size from 0.75 to 1 mm and constituting from 2 to 30 percent by weight of the catalyst and at least one of the layers of silver crystals constituting the upper or front region of the catalyst facing the mixture to be oxidized containing particles of size from 0.2 to 0.75 mm and constituting from 13 to 68 percent by weight of the catalyst.

* * * * *